United States Patent [19]

Golovchinskaya et al.

[11] 4,147,867
[45] Apr. 3, 1979

[54] 2-DIMETHYLAMINO-6-DIE-THYLENIMIDOPHOSPHAMIDO-7-METHYL-PURINE

[76] Inventors: Elena S. Golovchinskaya, B. Cherkizovskaya ulitsa, 5, korpus 1, kv. 283; Vladimir A. Chernov, Komsomolsky prospekt, 44, kv. 72; Elena S. Chaman, Leninsky prospekt, 70/11, kv. 300; Ljudmila A. Nikolaeva, ulitas Vinokurova 12, korpus 2, kv. 15; Vyacheslav S. Korsunsky, I Kozhukhovsky proezd 19, kv. 56, all of Moscow, U.S.S.R.

[21] Appl. No.: 727,515

[22] Filed: Sep. 28, 1976

Related U.S. Application Data

[60] Continuation of Ser. No. 603,387, Aug. 11, 1975, abandoned, which is a continuation of Ser. No. 500,557, Aug. 26, 1974, abandoned, which is a division of Ser. No. 339,346, Mar. 8, 1973, abandoned.

[51] Int. Cl.$^2$ .................. C07F 9/65; A61K 31/41
[52] U.S. Cl. ..................................... 544/244; 424/200
[58] Field of Search ................. 260/252; 424/200; 544/244

[56] References Cited

U.S. PATENT DOCUMENTS

| 2,663,705 | 12/1953 | Parker et al. | 200/268 K |
| 3,114,751 | 12/1973 | Whetstone | 260/252 |
| 3,666,748 | 5/1972 | Honjo et al. | 260/252 |

FOREIGN PATENT DOCUMENTS

| 2311905 | 9/1974 | Fed. Rep. of Germany | 544/244 |
| 1368049 | 9/1974 | United Kingdom | 544/244 |

OTHER PUBLICATIONS

Elderfield, vol. 8, "Heterocyclic Compounds", pp. 288 and 302 (1967).

Primary Examiner—Paul M. Coughlan, Jr.
Assistant Examiner—D. B. Springer
Attorney, Agent, or Firm—Holman & Stern

[57] ABSTRACT

2-Dimethylamino-6-diethylenimidophosphamido-7-methylpurine having the formula

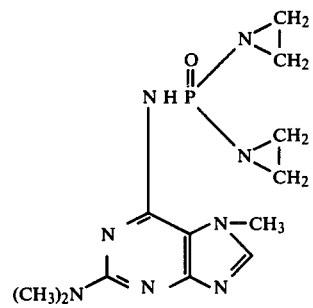

A method for preparing 2-dimethylamino-6-diethylenimido-phosphamido-7-methylpurine consisting of treating theobromine with heating to the boiling point and subsequently with phosphorus oxychloride and phosphorus pentachloride. The prepared 2,6-dichloro-7-methylpurine is heated to 50°–60° C. in an aqueous solution of ammonia and the resulting 2-chloro-6-amino-7-methylpurine is reacted, with heating, with an aqueous solution of dimethylamine. The obtained 2-dimethylamino-6-amino-7-methylpurine is reacted, at the boiling point, with either phosphorus oxychloride, or phosphorus pentachloride and formic acid. The resulting 2-dimethylamino-7-methylpurinyl-6-aminophosphoric dichloroanhydride is then treated with ethylenemine in a medium of an organic solvent in the presence of an acceptor of hydrogen chloride, and the final product is then isolated.

A preparation for treating malignant tumours of the haemopoietic system containing 2-dimethylamino-6-diethyleneimidophosphamido-7-methylpurine as the active principle is provided.

1 Claim, No Drawings

2-DIMETHYLAMINO-6-DIETHYLENIMIDO-PHOSPHAMIDO-7-METHYL-PURINE

This is a continuation of application Ser. No. 603,387 filed Aug. 11, 1975 which in turn is a continuation of application Ser. No. 500,557 filed Aug. 26, 1974 which in turn is a divisional of application Ser. No. 339,346 filed Mar. 8, 1973, all of which are now abandoned.

The present invention relates to a new substance, namely 2-dimethylamino-6-diethylenimidophosphamido-7-methylpurine, and a method for preparing same and to a medicinal preparation based on this substance.

The said substance, according to the invention, has the following formula:

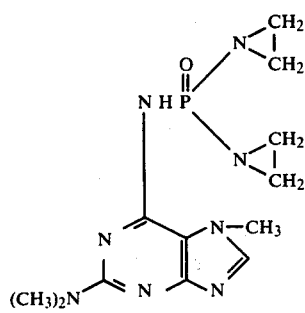

The proposed new compound is a colorless substance, soluble in water to a limited extent, readily soluble in chloroform, and also in boiling alcohol (1:5), toluene (1:70), benzene (1:70) and dichloroethane (1:6).

The substance has no definite melting point and is decomposed gradually at temperatures above 250° C.

2-Dimethylamino-6-diethyleneimidophosphamido-7-methyl-purine has cancerolytic activity and can therefore be used in medicine as a preparation against malignant growths in the haemopoietic system.

Preparations are known in the prior art which are preparations used for the said purposes, for example, thiophosphamide, dipin, and others, the cancerolytic properties of which are due to the presence of ethyleneimine groups.

However, these preparations have insufficient selectivity for their action on tumor tissue. Their anti-tumoric effect is only transient and can be observed only with doses that produce side effects.

According to the invention, the method for preparing 2-dimethylamino-6-diethylenemidophosphamido-7-methylpurine consists heating theobromine to the boiling point, and subsequently treating same with phosphorus oxychloride and phosphorus pentachloride, thus forming 2,6-dichloro-7-methylpurine which is heated to from 50° to 60° C. in an aqueous solution of ammonia, and the resulting 2-chloro-6-amino-7-methylpurine is heated and reacted with an aqueous solution of dimethylamine, and the thus formed 2-dimethylamino-6-amino-7-methylpurine is then reacted with phosphorus oxychloride or with phosphorus pentachloride and formic acid at the boiling point temperature, with subsequent processing of thus formed 2-dimethylamino-7-methylurinyl-6-amidophosphoric dichloroanhydride with ethyleneamine in organic solvent medium in the presence of a hydrogen chloride acceptor, and then isolating of the final product.

Chloroform, benzene, dichloroethane and ethylene chloride are used as the organic solvent in isolating the final product.

As was mentioned above, 2-dimethylamine-6-diethyleneimidophosphamido-7-methylpurine is the active principle of a new preparation which is used in medicine as a remedy against malignant tumors of the haemopoietic system.

The new preparation is given the name 'phopurine'.

Phopurine can be given to patients in the powder form (lyophilized on a 5 percent vinylpyrrolidone). When given intravenously or intramuscularly, it is recommended that the preparation containing the said active principle be used with a pharmaceutical solvent or carrier.

An isotonic solution of sodium chloride or distilled water can be used as the pharmaceutical solvent for the new preparation.

It is recommended that a from 0.1 to 1 percent solution of the new preparation in a pharmaceutical solvent be used.

The injection solution should be prepared just before injection by dissolving the sterile powder of 2-dimethylamino-6-diethyleneimidophosphamido-7-methylpurine in distilled water or in an isotonic solution of sodium chloride.

While studying the anti-tumor activity of the new preparation on animals, we established that it possesses a remarkable power to inhibit growth of many tumors grafted on rats and mice. Jensen's sarcoma strain appeared to be the most sensitive towards the action of phopurine. The administration of a single dose of 60 mg per kg body weight inhibited the growth of the tumor 95 percent.

A marked anti-leukemic activity of phopurine was noted in mice of the $C_{57}$ line with transplanted La leukemia. In all experiments, the animals to which the preparation was given, lived 2-3 times longer than the untreated animals.

Phopurine is superior to many other derivatives of ethylenimine, e.g., thiophosphamide, dipin, etc., with respect to its anti-tumor activity.

The data on the anti-tumoric effect of phopurine, thiophosphamide and dipin on the life duration of mice with La leukemia are given in the Table below

| Preparation | Maximum duration of life, in % to control |
|---|---|
| Thiophosphamide | 20 |
| Dipin | 56 |
| Phopurine | 204 |

The haematological indices also show the favorable course of the transplanted La leukemia in mice which underwent therapy with the preparation. The total quantity of leukocytes in mice with La leukemia almost did not differ from the starting counts in the end of the experiment with the phopurine therapy, while in control mice with leukemia, the leukocyte count increased significantly by the end of life. The quantity of immature forms in the controls increased sharply by the end of the experiment, while in the phopurine experimental animals this increase was insignificant.

Unlike the other derivatives of athylenimine, phopurine does not produce profound leukopenia in animals treated with the preparation.

It has been established that phopurine is less toxic than thiophosphamide or dipin. The cumulative properties of phopurine are less pronounced: the cumulative index of phopurine are less pronounced: the cumulative index of phopurine is 4 times less than in thiophosphamide and 7 times less than in dipin.

Phopurine acts in biological systems as an alkylating cytostatic preparation. When given in small doses, the preparation selectively inhibits the proliferating processes in tissues, including tumor tissues. Like other alkylating substances, phopurine reacts the nucleic centres of nucleic acids molecules and protein and alters various cell functions. The administration of the preparation in large tolerated doses produces a more significant destroying action on the tumor cells as compared with the action on the intact tissue cells, which is the essence of the anti-tumoric action of the proposed preparation.

Phopurine is dispensed in 0.04 g doses in sterile vials. The preparation should be stored in cool dark premises. The expiration term is one year (and over).

The method for preparing 2-dimethylamino-6-diethyleneimidophosphamide-7-methylpurine, which is the active principle of the preparation phopurine, should be effected preferably as follows:

Theobromine is boiled with excess phosphorus oxychloride until a solution is formed. Phosphorus pentachloride is added thereto and the resultant solution is boiled for from 10 to 12 hours in order ensure its complete dissolution. The reaction mass is then cooled, passed through a filter, and the separated precipitate (without drying or purification) is transferred with stirring into a cooled (5°–10° C.) aqueous solution of ammonia and then heated to from 50° to 60° C. in the presence of n-butyl alcohol (to prevent foaming) for from 10 to 12 hours. The thus formed product is separated and (without purifying) heated with an excess of a 33 percent aqueous solution of dimethylamine with a subsequent cooling and filtering.

The prepared 2-dimethyl-6-amino-7-methylpurine is purified by recrystallization from an aqueous alcohol solution and the purified product is then phosphorylated by two methods, either by phosphorus oxychloride or by phosphorus pentachloride and formic acid. In the former case, it is boiled with an excess quantity of phosphorus oxychloride for 8 hours, then phosphorus oxychloride is removed by vacuum distillation at 45°–50° C. and the crystalline precipitate is mixed thoroughly with dry toluene which is then removed (together with residual POCl3) by vacuum distillation.

According to the other method, 2-dimethyl-amino-6-amino-7-methylpurine is boiled in chloroform with a pre-calculated quantity of phosphorus pentachloride for about 5 hours until the hydrogen chloride stops evolving; the solution is then cooled and a pre-calculated quantity of formic acid is added slowly with stirring at a temperature at 20° C. The mixture is boiled for one hour, and chloroform and hydrogen chloride are in vacuum distilled.

An organic solvent, preferably chloroform, is added to the product prepared by either method, and then a mixture of ethylenimine and postassium carbonate (aqueous solution) is added slowly to the resultant suspension. The reaction mixture is stirred for 30 minutes at 20° C., and the chloroform layer is separated, dried and evaporated in a vacuum at a temperature of about 35° C. The residue is purified by crystallization first from alcohol and then from toluene, and the pure 2-diemthylamino-6-diethylenimidophosphamido-7-methylpurine is finally prepared.

Sodium bicarbonate, triethylamine, etc, can also be used as acceptors of a hydrogen chloride (instead of potassium carbonate).

For a better understanding of the invention, the following examples of preparing 2-dimethylamino-6-diethyleneimidophosphamide-7-methylpurine are given hereinbelow by way of illustration.

EXAMPLE 1.

(a) 200 g of theobromine are boiled with 1000 ml of phosphorus oxychloride for from 9 to 10 hours, and cooled, and boiled again in the prepared solution with 464 g of phosphorus pentachloride for another from 10 to 12 hours. The precipitate is separated and transferred immediately into a mixture of 2 liters of a 25 percent solution of ammonia in water and 1 kg of ice, and then heated from 50° to 60° C. for 10–12 hours in the presence of 60 ml of n-butyl alcohol, and the reaction mixture is passed through a filter, and the precipitate washed with water in order to prepare 218 g (146,5 g as dry product) of 2-chloro-6-amino-7-methylpurine.

The phosphorus oxychloride is removed from the mother liquor by distillation, and used in the next cycle without any purification. The still residue contains about 5 percent of 2-chloro-6-amino-7-methylpurine which should be recovered.

The moist 2-chloro-6-amino-7-methylpurine (218 g) prepared in mixed with 1500 ml of a 33 percent aqueous solution of dimethylamine and stirred at 65°–75° C. for 5–6 hours. The dimethylamine solution is distilled off (about 600 ml), and the residue cooled, and passed through a filter, and crystallized from 1100 ml of a 80 percent alcohol solution. The yield of the 2-dimethylamino-6-amino-7-methylpurine is 96.5 g. The melting point is from 280° to 284° C.

Calculated, in percent: C 50.0; H 6.25; N 43.75; $C_8H_{12}N$. Found, in percent: C 49.65; H 6.01; N 43.78.

(b) 96.5 g of 2-dimethylamino-6-amino-7-methylpurine are boiled with 500 ml of phosphorus oxychloride with stirring for eight hours. The phosphorus oxychloride is distilled, and the residue mixed with 600 ml of dry toluene; the toluene is distilled in vacuum, and 2 ml of chloroform is added to the residue and mixed. Now (with cooling to from 5° to 10° C.) a mixture of 57.9 ml of ethylenimine is added along with a solution of 104 g of potassium carbonate in 520 ml of water to the suspension which is mixed for thirty minutes at 20° C. The chloroform layer is separated, dried, evaporated, and the residue is crystallized first from alcohol (1:5) and then from toluene (1:70). The yield of the doubly-crystallized 2-dimethyl-amino-6-diethyleneimidophosphamido-7-methylpurine is 31–32 percent.

Calculated, in percent: C 44.72; H 5.90; N 34.78; P 9.62; $C_{12}H_9N_8OP$. Found, in percent: C 44.69; H 5.78; N 34.69; P 9.57.

EXAMPLE 2

96.5 g of 2-dimethylamino-6-amino-7-methylpurine prepared by the procedure described in item (a), Example 1 are boiled for 5 hours with 104 g of phosphorus pentachloride in 1000 ml of dry alcohol-free chloroform.

19.3 ml of formic acid are added to the solution at 60° C., and boiled for one hour, after which it is evaporated in a vacuum at from 30° to 40° C. 2 liters of chloroform are added to the residue, and then, with energetically stirring, at from 5° to 10° C., add a mixture of 57.9 ml of ethylenimine and 104 g of potassium carbonate solution a in 520 ml of water are added thereto and mixed for thirty minutes. The chloroform is separated from the solution, dried, and the chloroform is distilled at about 35° C. The residue is crystallized first from alcohol (1:5) and then from toluene (1:70). The yield of the doubly crystallized 2-dimethylamino-6-diethyleneimidophosphamido-7-methylpurine is 31–32 percent.

What we claim is:

1. 2-dimethylamino-6-diethyleneimidophosphamide-7-methylpurine having the formula

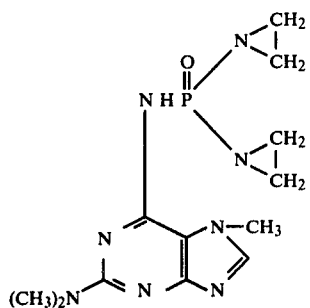

* * * * *